United States Patent
Hill et al.

[11] Patent Number: 5,944,524
[45] Date of Patent: Aug. 31, 1999

[54] BIOHYBRID DENTAL IMPLANT

[75] Inventors: Frank Hill, deceased, late of Mettmann, by Hella Luise Hill, heiress, Henning Hinrich Hill, heir, Friedrich Frank Hill, heir, Regina Luise Hill, heiress; Fritz Schindler, Gelsenkirchen; Hugo Haemmerle, Tuebingen; Lutz Scheideler, Bonn, all of Germany

[73] Assignee: Huels Aktiengesellschaft, Marl, Germany

[21] Appl. No.: 08/864,722

[22] Filed: May 28, 1997

[30] Foreign Application Priority Data

Jul. 25, 1996 [DE] Germany .......................... 196 30 034

[51] Int. Cl.$^6$ .............................. A61C 8/00; A61L 27/00; C12N 11/02
[52] U.S. Cl. .......................... 433/173; 433/201.1; 623/16
[58] Field of Search ..................................... 433/173, 174, 433/175, 176, 201.1; 623/16

[56] References Cited

U.S. PATENT DOCUMENTS

| | | |
|---|---|---|
| 4,609,551 | 9/1986 | Caplan et al. . |
| 4,812,120 | 3/1989 | Flanagan et al. ........................ 433/173 |
| 4,957,509 | 9/1990 | Tamari et al. . |
| 5,178,901 | 1/1993 | Toriyama et al. . |
| 5,217,496 | 6/1993 | Bruce et al. .............................. 623/16 |
| 5,306,305 | 4/1994 | Lee ........................................... 623/16 |
| 5,700,289 | 12/1997 | Breitbart et al. .......................... 623/16 |
| 5,772,439 | 6/1998 | Yamaoka et al. ....................... 433/173 |

FOREIGN PATENT DOCUMENTS

| | | |
|---|---|---|
| 0 205 333 | 12/1986 | European Pat. Off. . |
| 0 263 088 | 4/1988 | European Pat. Off. . |
| 0 530 458 | 3/1993 | European Pat. Off. . |
| 0 555 760 | 8/1993 | European Pat. Off. . |
| 38 31 260 | 3/1989 | Germany . |
| 40 40 872 | 7/1992 | Germany . |
| 42 22 296 | 12/1993 | Germany . |
| WO 92/22335 | 12/1992 | WIPO . |

OTHER PUBLICATIONS

M. Nakashima, Archs Oral Biol., vol. 35, No. 7, pp. 493–497, 1990, "The Induction of Reparative Dentine in the Amputated Dental Pulp of the Dog by Bone Morphogenetic Protein".

Hideaki Nakae, et al., Biochemistry, vol. 30, No. 29, pp.7047–7052, 1991, "Isolation and Partial Characterization of Mitogenic Factors From Cementum".

Patricia A. Parsons–Wingerter, et al., Biotechnol. Prog., vol. 9, No. 6, pp. 600–607, 1993, "Growth Versus Function in the Three–Dimensional Culture of Single and Aggregated Hepatocytes Within Collagen Gels".

Database WPI, Derwent Publications, AN 91–234083/32, JP 3–151978, Jun. 28, 1991.

Database WPI, Derwent Publications, AN 88–170090/25, JP 63–105765, May 11, 1988.

*Primary Examiner*—Ralph A. Lewis
*Attorney, Agent, or Firm*—Oblon, Spivak, McClelland, Maier & Neustadt, P.C.

[57] ABSTRACT

A dental implant coated with a composition containing desmodontal cells, where the cells are not propagated in vitro prior to being coated on the implant.

21 Claims, No Drawings

BIOHYBRID DENTAL IMPLANT

BACKGROUND OF THE INVENTION

1. Field of the Invention

The present invention relates to a dental implant coated with a composition containing periodontal cells, where the cells are not propagated in vitro prior to coating the implant.

2. Discussion of the Background

Teeth are elastically suspended in the jawbone via a retaining element consisting of collagen fibers, i.e., the periodontal ligament. The elasticity of the retaining apparatus is important for providing flexible adaptation to a variety of different chewing stresses on the teeth.

The dental implants generally used today are anchored firmly to the jawbone and, therefore, are foreign to the natural teeth-retaining element discussed above. Most of these implants are pins or screws made of titanium, coated titanium or a ceramic material, which support an artificial tooth structure which replace a natural tooth.

These conventional implants are usually inserted by a dentist in a hole drilled in the jawbone and then mechanically fastened therein. After implantation in the jawbone, the implant undergoes osseous integration into the jawbone. The bone grows around the implant, envelops it and holds it firmly. This rigid integration into the jawbone contrasts with the elastic suspension of the natural tooth. Problems and complications occur in particular:

when the implant is removed, as occasionally becomes necessary, it is necessary to use a bone cutter, which causes local damage to the jaw;

when there are bridge constructions between the implant and natural tooth, the rigid implant and the movable natural tooth have limited compatibility as supporting elements for a bridge; and during chewing where rigid integration into the jawbone impairs bite sensitivity.

In addition, in some cases the implant fails to integrate into the jawbone and there is partial regression of the jawbone as a result of nonphysiological stresses. To overcome these problems, special coatings for the implants which promote osseointegration have been developed, see, for example:

U.S. Pat. No. 4,957,509: coatings with zirconium nitride, silicon nitride or silicon carbide U.S. Pat. No. 5,178,901: coating with a ceramic CaO/$TiO_2$/$P_2O_5$/$Na_2O$ composition JP 3 151 978: $Al_2O_3$/$ZrO_2$ ceramic WO 9 222 335: Coating with calcium phosphate which has been converted by a hydrothermal treatment into hydroxyapatite EP 0 205 333: coating with hydroxyapatite-containing polymethacrylate DE 38 31 260: sintering on hydroxyapatite/tricalciumphosphate with subsequent acid treatment results in a porous hydroxyapatite layer.

DE 40 40 872 and DE 42 22 296 disclose implants for dentistry, where human periodontal fibroblasts are taken from extracted tooth roots, propagated in vitro for several weeks, and then transferred to the implant shortly before insertion of the implant. However, this in vitro propagation step precludes obtaining the fibroblasts from a patient and inserting the coated implant in one treatment session.

Accordingly, there remains a need for cell-coated dental implant which does not require in vitro cell propagation.

SUMMARY OF THE INVENTION

It was an object of the present invention to provide a dental implant coated with periodontal fibroblasts which integrates into the jawbone and does not require in vitro propagation of the fibroblasts.

The above objects and others may be accomplished with a dental implant coated with a composition containing desmodontal cells and a desmodontal cell-stimulating agent, wherein the desmodontal cells have not been propagated in vitro.

The above objects may also be accomplished by a method of making a dental implant coated with desmodontal cells where the cells are isolated and coated on the implant without the need for an in vitro propagation step.

The above objects may also be accomplished with a method for implanting a dental implant in which desmodontal cells are isolated from a patient, a dental implant is coated with the cells and then the implant is implanted in the patient, all in one treatment session.

A more complete appreciation of the invention and many of the attendant advantages thereof will be readily obtained as the same becomes better understood by reference to the following detailed description.

DETAILED DESCRIPTION OF THE INVENTION

During investigations relating to the present invention, a dental implant has been developed which, by use of specially treated implant surfaces and stimulants, especially of mitosis stimulants, promotes periodontal fibroblasts propagation significantly faster than in the untreated state. The stimulation of cell activity is, surprisingly, so great that it is possible to use the stimulants and dispense with the in vitro propagation step, as described in DE 40 40 872 and DE 42 22 296, of the periodontal fibroblasts prior to colonization of the implants by these cells. With the present invention it is possible, in one treatment session, to:

extract a diseased or dead tooth;

colonize a dental implant with periodontal fibroblasts obtained, for example, by excision of a sample or taken from desmodontal tissue from an extracted tooth; and insert the implant.

Important features of the present invention include:

colonizing the implant surfaces with the cells which form the collagen fibers of the natural teeth retaining element (periodontal fibroblasts and other desmodontal cells), creating conditions which stimulate the cells, and using implants which have surfaces that are compatible with cell colonization and cell stimulation.

In contrast to DE 40 40 872 and DE 42 22 296, the in vitro propagation phase of several weeks for the desmodontal cells is unnecessary, and extraction of a decayed or diseased tooth may be performed together with insertion of the implant in one treatment session. As used herein, the term "one treatment session" refers to a visit to the dentist by a patient in one day. Accordingly, a treatment session preferably has a duration of at most 24 hours, more preferably at most 15 hours, even more preferably at most 10 hours and most preferably at most 6 hours. A treatment session may even have a duration of less than 6 hours, such as 1 to 5 hours.

An important feature of the present invention is coating a dental implant with a composition containing desmodontal cells and stimulants. The coating composition is preferably a gel which may be prepared by:

proteolytic treatment of a desmodontal tissue obtained, for example, by excision of a sample or by scraping off an extracted tooth root, with collagenase and/or trypsin and/or other enzymes. The proteolytic treatment breaks down the tissue structure. It is also possible, as an alternative to the proteolytic treatment, or, in combination with it, to comminute the desmodontal tissue mechanically;

optionally, concentration and washing of the resulting cell suspension or tissue suspension by centrifugation;

addition of blood plasma or serum or of cell growth hormones such as EGF and/or BMP and/or other factors with mitogenic activity to the desmodontal cells;

optionally, addition of one or more antibiotics;

optionally, addition of a gel-forming substance in the form of a solution or as soluble substance; and optionally, addition of an inorganic substance which induces and/or stabilizes gel formation or otherwise has a beneficial effect on development of the natural tooth retaining apparatus.

With the present process, the desmodontal cells may be freshly isolated from, for example, a patient after removal of a tooth, and then used to coat the implant within a short period of time. There is no need for in vitro propagation of the cells, therefore, such a step is preferably excluded from the present method. In the present invention, the amount of time between isolating the cells, preparing the coating composition and coating the implant may be at most 24 hours, preferably at most 12 hours, more preferably at most 8 hours, even more preferably at most 6 hours and, most preferably, at most 4 hours. This length of time may be even shorter than 4 hours, such as 1 to 3 hours.

In addition to the desmodontal cells, the coating composition may further contain the following components:

(A) a gel-forming substance, (B) one or more substances with antibiotic activity, (C) factors which have been purified or are in the form of a complex mixture, and which stimulate cellular activity, and (D) inorganic substances.

The nature of the gel-forming substance (A) is not particularly limited. Suitable examples of the gel forming substance include collagen, fibrinogen, aprotinin and/or sodium alginate.

Component (B) comprises antibiotics from the class of penicillins, cephalosporins, streptomycins, ciprofioxacins, tetracyclines and/or erythromycins. Preferably, the concentration of antibiotic is 10–1,000 µg per ml or 10–1,000 I.V. per ml.

The stimulating factors (C) used in the composition may be pure proteins. Suitable proteins include epidermal cell growth factors and/or bone morphogenic proteins. The stimulating factors may also be in the form of a complex extract of juvenile tooth buds from agricultural animals or a serum from agricultural animal fetuses. Mixtures of these factors may be used.

The inorganic substances (D) may be any inorganic material well-known to those of ordinary skill in the art for dental applications. Preferred inorganic substances are inorganic salts. Calcium phosphate and, more preferably, hydroxyapatite may be used as substance (D).

The composition may be applied to the implant in any effective amount. The composition is preferably applied in a layer 0.1–2 mm thick on surface of the implant.

The core of the implant may be made of any of the materials well-known to those of ordinary skill in the art.

The core is preferably a hard material. Titanium or a titanium-based alloy are the preferred materials for the core.

The core is preferably covered with a surface suitable for colonization by the desmodontal cells and for anchoring the collagen fibers to be formed by these cells, i.e., a biocompatible covering. Examples of suitable biocompatible coverings include a PMMA/collagen composite material disclosed in German Patent Application "Biokompatibles Verbundmaterial und Verfahren zu seiner Herstellung" (Application No. 195 29 036.4, incorporated herein by reference) and silicon carbide. A silicon carbide covering is preferably produced by coating an artificial tooth root which comprising titanium or an alloy thereof with a silicon-containing paste, and then decomposing the paste at temperatures <1,000° C. and subsequently at temperatures >1,400° C.

Having generally described this invention, a further understanding can be obtained by reference to certain specific examples which are provided herein for purposes of illustration only and are not intended to be limiting unless otherwise specified.

EXAMPLES

Example 1. Production of Implants Coated with Silicon Carbide

A flour paste containing 30% flour and 70% silicon powder was stirred with water to form a pasty slurry and applied to a titanium pin which was intended to be used as artificial tooth root. As disclosed in EP 0 555 760, incorporated herein by reference, this composition was decomposed at a temperature of 200–800° C. for 1–2 h and subsequently converted into SiC at a reaction temperature of >1,400° C. for 1–2 h. A metal pin resulted with a rough finished surface comprising silicon carbide and able to bind newly formed collagen proteins and thus assist the development of the fibrillary structure of the periodontium.

Example 2. Preparation of a Gel Containing Live Desmodontal Cells and Stimulants The desmodontal tissue was scraped off with a scalpel from a freshly extracted tooth and taken up in a few ml of Eagle's Minimum Essential Medium (MEM) with the addition of 30% fetal calf serum. After addition of trypsin and/or collagenase, this mixture was incubated with shaking at 37° C. for about 1 h, during which the suspension was converted from pieces of desmodontal tissue into a suspension of isolated cells. To remove excess enzyme, the cell suspension was filtered through a net with meshes 50 µm wide and subsequently centrifuged at 150 rpm for 5 minutes. The cell-containing sediment afforded, after washing twice in a few ml of the stated medium (MEM+30% fetal calf serum), a few ml of medium with isolated and substantially purified desmodontal cells.

Addition of antibiotics

Antibiotics were added to the cell suspension in an effective amount to prevent sepsis for several days, even taking account of the diffusion losses after implantation of the artificial tooth root covered with the gel. Particularly suitable antibiotics were penicillin and streptomycin, and other, mainly lipophilic, antibiotics.

Addition of growth factors

In addition, adequate amounts of the commercially available epidermal growth factor or the growth factor which can be isolated by the method of Nakae et al. (isolation and partial characterization of mitogenic factors from cementum (see, Biochemie 30, 7047–7052 (1991), incorporated herein by reference) was added to the cell suspension. Other purified growth factors which can be added are the morphogenic bone growth factor of Nakashima (Arch Oral. Biol. 35, 493–497 (1990), incorporated herein by reference) or an extract from juvenile tooth buds of agricultural animals (EP 0 263 088, incorporated herein by reference). It may be advantageous to add dextran or calcium phosphate together with the growth factors in order to achieve a release-slowing effect (EP 0 530 458 and JP 6 3105765, both incorporated herein by reference).

Production of the gel

The cell suspension containing the active substances was converted into a gel in several ways:

addition of fibrinogen, thrombin and aprotinin, addition of collagen as disclosed by Parson-Wingerter and Saltzman (Biotechnol. Prog. 9, (1993), pages 600–607, incorporated herein by reference), addition of a mixture of collagen and calcium phosphate, addition of sodium alginate and subsequent induction of gel formation by addition of $CaCl_2$, Covering of the implant with the gel The implant was covered with the gel in a layer 0.1–2 mm thick, with, for example, the aid of a spatula.

Example 3. Simplified Process for Preparing an Implant

Pieces of desmodontal tissue were obtained by excision of a sample or from the desmodontal tissue from an extracted tooth and then mechanically comminuted and washed in a buffer solution. The supernatant washing solution was drawn off and the remaining pieces of tissue were suspended in culture medium containing growth factors and/or fetal calf serum and antibiotics, and subsequently mixed with a gel-forming mixture.

The gel-forming mixture was prepared as follows. A solution of collagen (1 to 20 mg of collagen per ml) in acetic acid (0.1 N) which had been cooled to 4° C. was adjusted to pH 7.4 with culture medium which had been made alkaline. The tissue suspension was added to this solution in the ratio of, preferably, 1 part of tissue suspension to 9 parts of gel-forming solution, and thoroughly mixed. The implant to be coated was then immersed in this suspension. After warming to room temperature, the suspension gelled within a few minutes and coated the immersed implant with a cell-containing gel layer.

Example 4. Implantation

The implant covered with the gel was placed in the empty alveolus or in a hole cut in the jaw and subsequently the flaps of gum were closed with a surgical suture. In the natural environment, proliferation of calls and formation of collagen fibers of the retaining apparatus began. It may prove beneficial or necessary to fit the crown onto the implant, and to stabilize it with a provisional splint or wire loop, after only 12–14 days. However, healing times of 4 to 8 weeks before the crown is fitted are preferred.

As an alternative to the procedure described above (load-free, mucosa-covered healing), the artificial tooth root may also be provided even before the implantation with a structure which projects through the mucosa into the oral cavity. The implant is fixed via this structure to the neighboring teeth in such a way that a defined, small range of movement is permitted (healing under defined load).

Obviously, numerous modifications and variations of the present invention are possible in light of the above teachings. It is therefore to be understood that within the scope of the appended claims, the invention may be practiced otherwise than as specifically described herein.

This application is based on German Patent Application No. 196 30 034.7, filed Jul. 25, 1996 and incorporated herein by reference in its entirety.

What is claimed as new and is desired to be secured by letters patent of the United States is:

1. A dental implant, comprising:
   a core;
   a biocompatible covering on said core; and
   a coating on said biocompatible covering, wherein said coating comprises desmodontal cells and at least one desmodontal cell-stimulating agent, and
   wherein said desmodontal cells have not been propagated in vitro.

2. The dental implant of claim 1, wherein said desmodontal cells are isolated by a process comprising treating desmodontal tissue with at least one proteolytic enzyme to produce a cell suspension comprising from $10^2$ to $10^6$ live cells per ml.

3. The dental implant of claim 1, wherein said desmodontal cells are obtained by a process comprising mechanically comminuting pieces of desmodontal tissue to produce a suspension comprising from $10^1$ to $10^3$ pieces of desmodontal tissue per ml.

4. The dental implant of claim 1, made by a process comprising:
   isolating desmodontal cells; and
   coating a dental implant with a composition comprising said desmodontal cells and at least one desmodontal cell-stimulating agent,
   wherein the total time between said isolating step and said coating step is at most 24 hours.

5. The dental implant of claim 1, wherein said coating comprises a gelling agent.

6. The dental implant of claim 5, wherein said gelling agent is selected from the group consisting of collagen, fibrinogen, aprotinin, sodium alginate and mixtures thereof.

7. The dental implant of claim 5, wherein said coating is prepared by a process comprising gelling freshly isolated desmodontal cells in a composition comprising a gelling agent.

8. The dental implant of claim 1, wherein said desmodontal cell-stimulating agent is selected from the group consisting of epidermal cell growth factors, bone morphogenic proteins, extracts from juvenile tooth buds of agricultural animals, serum from agricultural animal fetuses and mixtures thereof.

9. The dental implant of claim 1, wherein said coating further comprises at least one antibiotic.

10. The dental implant of claim 9, wherein said antibiotic is selected from the group consisting of penicillins, cephalosporins, streptomycins, ciprofloxacins, tetracyclines, erythromycins and mixtures thereof; and the concentration of said antibiotic in said coating is either 10–1,000 $\mu$g per ml or 10–1,000 I.U. per ml.

11. The dental implant of claim 1, wherein said coating further comprises an inorganic salt selected from the group consisting of calcium phosphate, hydroxyapatite and mixtures thereof.

12. The dental implant of claim 1, wherein said core comprises titanium or an alloy thereof.

13. The dental implant of claim 1, wherein said biocompatible covering comprises silicon carbide or a PMMA/collagen composite material.

14. The dental implant of claim 1, wherein said desmodontal cells are fibroblasts.

15. A method of making a cell-coated dental implant, comprising:

coating a dental implant with a composition comprising desmodontal cells and at least one desmodontal cell-stimulating agent, wherein said desmodontal cells are not propagated in vitro prior to said coating step.

16. The method of claim 15, further comprising prior to said coating step:

isolating desmodontal cells, wherein the total time between said isolating step and said coating step is at most 24 hours.

17. The method of claim 15, wherein said desmodontal cells are fibroblasts.

18. A method of implanting a dental implant, comprising:

isolating desmodontal cells from a patient;

coating a dental implant with said desmodontal cells;

implanting the coated dental implant in said patient, wherein said desmodontal cells are not propagated in vitro after said isolating step.

19. The method of claim 18, wherein said isolating, coating and implanting steps are conducted in one treatment session.

20. The method of claim 18, wherein the length of said treatment session is at most 24 hours.

21. The method of claim 18, wherein said desmodontal cells are fibroblasts.

* * * * *